United States Patent [19]

Fischer et al.

[11] 4,252,901

[45] Feb. 24, 1981

[54] SYSTEM AND PROCESS FOR ANAEROBIC DIGESTION

[75] Inventors: David J. Fischer; Richard M. Narske; John C. Thomas; Edward J. Worthington, Jr., all of Sarasota, Fla.

[73] Assignee: Universal Research and Development Corp., Tallevast, Fla.

[21] Appl. No.: 56,545

[22] Filed: Jul. 11, 1979

[51] Int. Cl.³ ............................ C12P 5/02; C12M 1/40
[52] U.S. Cl. ..................................... 435/167; 48/197 A; 71/10; 210/603; 435/174; 435/288; 435/801; 435/819
[58] Field of Search ................. 48/111, 197 A; 71/10; 55/73; 210/2, 6, 10, 11, 12, 16, 18, 42 S, 47, 73 S, 96.1; 435/166, 167, 174, 288, 291, 801, 807, 819

[56] References Cited

U.S. PATENT DOCUMENTS

| | | | |
|---|---|---|---|
| 1,420,250 | 6/1922 | Gavett | 210/2 |
| 2,029,702 | 2/1936 | Buswell et al. | 435/819 |
| 3,156,646 | 11/1964 | Cameron | 210/16 |
| 3,259,566 | 7/1966 | Torpey | 210/10 |
| 3,362,887 | 1/1968 | Rodgers | 201/2.5 |
| 3,664,951 | 5/1972 | Armstrong | 210/96.1 |
| 3,774,760 | 11/1973 | Beristain et al. | 210/73 SG |
| 3,962,069 | 6/1976 | Inoue et al. | 210/47 |
| 3,981,800 | 9/1976 | Ort | 210/6 |
| 4,022,665 | 5/1977 | Ghosh et al. | 435/801 |
| 4,040,953 | 8/1977 | Ort | 48/197 A |
| 4,046,551 | 9/1977 | Anderson | 71/10 |
| 4,057,401 | 11/1977 | Boblitz | 48/111 |
| 4,130,403 | 12/1978 | Cooley et al. | 55/73 |
| 4,148,731 | 4/1979 | Brigante | 210/425 |

Primary Examiner—Peter A. Hruskoci
Attorney, Agent, or Firm—Benjamin P. Reese, II

[57] ABSTRACT

A system and a process for producing methane gas by anaerobic digestion of feed materials containing suitable organic materials. The system includes a plurality of digestion modules arranged primarily in series. Each digestion module is positioned with its slurry inlet port at a slightly lower elevation than the slurry outlet port of the preceding digestion module. The number of digestion modules is dependent upon the particular feed material to be digested. Each digestion module can be sampled and controlled independently. The process includes grinding and pulping the feed material, mixing the feed material with a liquid to prepare a slurry, charging the initial digestion module with slurry and transferring the digesting slurry to the next successive digestion module and subsequently to each successive digestion module after predetermined time periods until the digestion process has been completed. The liquid is separated from the digested slurry for recycle through the system. The resulting sludge is useful for a variety of purposes.

6 Claims, 5 Drawing Figures

SYSTEM AND PROCESS FOR ANAEROBIC DIGESTION

BACKGROUND OF THE INVENTION

This invention relates to a system and process for production of methane gas by anaerobic digestion of feed materials containing suitable organic materials.

It is well known that suitable organic materials will decompose or decay by either aerobic (with oxygen) or anaerobic (without oxygen) processes. Both aerobic decomposition and anaerobic decomposition are naturally occurring biochemical processes. Since early times, man has exploited aerobic decomposition to produce compost for fertilizing his crops. Typically, compost production was accomplished with a compost pile. While some anaerobic decomposition always occurred in the compost pile, man did not begin to understand anaerobic decomposition and control it for useful purposes until the present century.

While either aerobic or anaerobic processes can be used for decomposing suitable organic materials, the resulting decomposition products will be quite different. If suitable organic materials are decomposed by an anaerobic process, both methane and carbon dioxide gases are produced. It is well known that methane is a colorless, odorless, tasteless, lighter-than-air gas which is useful as a fuel. In fact, methane is a principal component of ordinary natural gas. In addition to the production of methane, a potentially valuable sludge is produced when sewage, animal manures and many other feed materials containing suitable organic materials are digested by an anaerobic process. Such sludge can be used as a soil conditioner or as a source of various inorganic or organic elements and compounds useful as raw materials for subsequent manufacturing processes.

If anaerobic processes are to be successfully exploited for useful purposes, it is desirable to have those processes take place in insulated, oxygen-free containers. When feed materials containing suitable organic materials are placed in such containers, it is possible to both mimic and hasten the naturally occurring biochemical processes. When feed materials containing suitable organic materials are processed under such conditions, the process is commonly referred to as "anaerobic digestion". The insulated, oxygen-free containers are commonly referred to as "digesters".

Most of the early research and development relating to anaerobic digestion was performed in India. It is usually believed that the first digester for production of methane gas by anaerobic decomposition of organic materials was constructed in Bombay, India in 1900. That digester utilized cow manure as a feed material for the anaerobic decomposition process. It is well known that the Indian economy was at that time and continues to be in large part agriculturally based. It has been estimated that for every person living in India there are two cows living there. Because of this large cow population, large quantities of manure are available in India as a feed material for production of methane gas by anaerobic digestion. The resulting methane gas is burned as a fuel for cooking, heating, lighting and powering farm equipment. And, the resulting sludge is used as a soil conditioner.

In India, the research and development activities relating to anaerobic digestion have concentrated on simple small-scale digesters for digestion of manures and other organic waste materials. Both batch load digesters, i.e. digesters which are charged with feed material, sealed for the digestion period, and then emptied when methane gas production ceases, and continuous load digesters, i.e. digesters which are charged with smaller quantities of feed material on a daily or other periodic basis and continuously produce methane gas, have been developed, constructed and operated. The primary objectives for these digesters have been to provide digesters which are capable of being constructed by unskilled laborers using inexpensive building materials indigenous to a rural agricultural environment and to provide digesters which are capable of being operated and maintained by farmers and unskilled laborers having minimal formal technical education. Of course, these objectives are compatable with the circumstances existing in India.

In the United States and in other countries having highly industrialized economies, waste materials have not traditionally been considered to be a national asset. Accordingly, research and development activities relating to waste materials have concentrated on environmentally safe disposal of such materials. Nevertheless, some research and development activities relating to the production of methane gas by anaerobic digestion of feed materials containing suitable organic materials have been conducted in the United States. Until recently, most of these activities were conducted and financed by persons who are proponents of alternate life styles for the United States population. For this reason, the objectives of the early United States research and development activities relating to anaerobic digestion were similar to the objectives of similar activities in India. Small scale digesters were constructed for production of methane by digestion of waste materials containing suitable organic materials. In a few cases, larger digesters have been constructed. But, all of these digesters have been similar to those used in India since 1900 and have been used exclusively for digestion of waste materials.

With the continuing upward spiral of prices for oil, natural gas, coal and nuclear fuels, it is desirable to have a system and process for production of the maximum quantity of methane gas which a particular feed material containing a suitable organic material is capable of yielding. Such a system and process should be capable of using any material containing suitable organic materials as the feed material for the system and process. For example, it may be desirable to grow and harvest certain plants specifically for feed materials for the system and process.

SUMMARY OF THE INVENTION

The present invention provides an improved system and process for production of methane gas by anaerobic digestion of feed materials containing suitable organic materials. The primary objective of the present invention is to provide a system and process for control and optimization of the various anaerobic decomposition process variables. With such control and optimization, it is possible to produce greater quantities of methane gas from a given quantity of organic material than can be produced by prior art anaerobic digesters and anaerobic digestion processes. Also, it is possible to complete the production of methane gas in a shorter period of time than is possible with prior art anaerobic digesters and anaerobic digestion processes. In addition, the system and process of the present invention can be adapted for efficient small, intermediate or large scale methane gas production operations.

It is anticipated that the system and process of the present invention can be used to produce methane gas by anaerobic digestion of any feed material containing suitable organic materials. In particular, vegetable by-products and waste from the farming and food products industries, various animal by-products and waste from the animal husbandry and food products industries, various waste materials from the chemical processing industries, sewage traditionally treated at municipal waste treatment facilities, and selected portions of the solid material from conventional municipal garbage disposal operations would be suitable feed materials for anaerobic digestion by the system and process of the present invention. Also, various plants, such as kelp, water hyacinths, grasses, grains and sugar beets, could be grown and harvested specifically as feed materials for production of methane gas by anaerobic digestion using the system and process of the present invention. The various anaerobic decomposition process variables would be appropriately adjusted to accommodate the particular feed material utilized.

To minimize feed material transportation costs, it is anticipated that the system of the present invention would be constructed and the process of the present invention practiced at or near the locations where suitable feed materials are available in large quantities. In particular, it would be desirable to construct the system and practice the process on or near one or more large farms or ranches. Other suitable locations include large industrial complexes, large single-family and multi-family housing developments, municipal garbage disposal dumps and municipal waste treatment facilities.

The methane gas produced by the system and process of the present invention can be burned at the production location to heat water for generation of steam. The resulting steam can be used to produce mechanical work for turning a conventional electrical generator to produce electricity for use at the production location or for transmission through a conventional power grid. And, of course, the methane gas so produced can be used as a direct energy source by burning it for lighting, cooking, space heating, water heating, clothes drying and similar purposes. If used as a direct energy course, the methane gas can be either used at its production location or transmitted through conventional gas pipelines for ultimate use. Furthermore, the methane gas can be pressurized and stored in conventional pressure vessels or tanks for ultimate use as a primary or auxiliary fuel for internal combustion engines, such as the type used to power automobiles, trucks, tractors, motorboats and other automotive vehicles.

While the production of useful solid materials is not the primary objective of the present invention, it is anticipated that the sludge resulting from anaerobic digestion of suitable feed materials using the system and process of the present invention would have significant economic value. For example, such sludge could be used as a soil conditioner or fertilizer. This would be particularly desirable if the system were constructed and the process were practiced at or near one or more large farms. Alternatively, such sludge could be used as a valuable source of various inorganic and organic elements and compounds useful as feed materials for subsequent manufacturing processes. In particular, it is anticipated that the sludge remaining after anaerobic digestion of municipal sewage and various industrial materials would contain economically recoverable quantities of several trace elements.

The system of the present invention is comprised of a feed material pre-treatment sub-system, a slurry preparation sub-system, an anaerobic digestion sub-system, a gas collection sub-system, a gas storage sub-system, a sludge separation sub-system and a particle separation sub-system. The anaerobic digestion sub-system is comprised of a plurality of individual digestion modules arranged to accommodate a multi-stage anaerobic digestion process. Each of the individual digestion modules is a conventional insulated, oxygen free reaction vessel or container. In general, the individual digestion modules are arranged in a series configuration. When it is desirable to have either a longer retention period or a greater slurry surface to volume ratio for a particular stage of the anaerobic digestion process, two or more digestion modules can be arranged in parallel to accommodate that stage of the process.

Since the system of the present invention is comprised of a plurality of individual digestion modules, a port for either sampling the digesting slurry or adding microbes, enzymes, catalysts and the like to the digesting slurry, or both, can be provided for each module. This enables the operator to obtain the information necessary to understand and control each stage of a multi-stage anaerobic digestion process and to take appropriate actions to control each such stage. With prior art digesters, it has not been possible either to obtain such sequential information for anaerobic digestion processes or to effectively control such processes.

The individual digestion modules provided in the system of the present invention provide a means for either immobilizing and retaining, or retaining previously immobilized, microbes and enzymes for enhancing methane gas production at particular stages of the anaerobic decomposition process. Porous organic or inorganic materials, or a suitable combination thereof, can be used for such purposes. The interior surface of a digestion module can be either treated or lined with such materials, or both. Alternatively, solid shapes of such materials can be placed inside the particular digestion module. This feature provides a means for controlling the anaerobic decomposition process which is not available with prior art digesters.

The preferred embodiment of the system of the present invention provides novel means for gravity transfer of the digesting slurry from one digestion module, or one group of digestion modules, to the next successive digestion module, or group of digestion modules. For this reason, it is not necessary to provide pumps for transferring the digesting slurry. And, no mechanical mixers are necessary for mixing the digesting slurry. Each individual digestion module, or each group of digestion modules, is positioned with its inlet port, or inlet ports, at a slightly lower elevation than the outlet port, or outlet ports, of the preceding digestion module, or group of digestion modules. In addition, each individual digestion module is positioned on a slight incline to provide for gravity flow of the digesting slurry in the module from the inlet port to the outlet port of that module.

It is anticipated that most of the carbon dioxide which is produced during the anaerobic digestion process of the present invention will be produced in the first several digestion modules. And, it is anticipated that most of the methane which is produced during the anaerobic digestion process of the present invention will be produced in the last several digestion modules. The gaseous product produced during the intermediate digestion modules is likely to be a mixture of both carbon dioxide and methane. For this reason, the present invention provides means for collecting the gases produced in each individual digestion module, or each group of digestion modules, without mixing those gases with gases produced in other modules, or groups of modules. Three separate gas storage locations are provided in the preferred embodiment. One location provides a means for storage of essentially pure carbon dioxide and another location provides a means for storage of essentially pure methane. The third location provides a means for storage of carbon dioxide-methane mixtures. In addition, a means for separation of carbon dioxide and methane for ultimate storage in the separate location for each is provided in the system of the present invention.

In the preferred embodiment of the process of the present invention, a suitable particulate material is added to the slurry in the slurry preparation sub-system. The particulate material absorbs and adsorbs methane as it is generated in the digesting slurry. When the anaerobic digestion process is completed, the particulate material is separated from the liquid effluent and outgased to collect the methane held by the particulate material. This feature of the invention helps to prevent mixing of the carbon dioxide and methane gases which are produced during the anaerobic digestion process, and thereby, substantially reduces the quantities of gases which must be separated. Means are provided for analyzing the dissolved solids content of the liquid effluent to provide the operator information necessary for optimization of liquid effluent recycle to the slurry preparation sub-system.

These and many other advantages, features and objects of the present invention will be apparent from the following brief description of drawings, description of the preferred embodiment and the appended claims.

DESCRIPTION OF THE PREFERRED EMBODIMENT

The anaerobic digestion system of the present invention is illustrated schematically in FIGS. 1-5. The system of the present invention is comprised of a feed material pretreatment sub-system, a slurry preparation sub-system, an anaerobic digestion sub-system, a gas collection sub-system, a gas storage sub-system, a sludge separation sub-system and a particle separation sub-system. The anaerobic digestion process of the present invention is a multi-stage anaerobic decomposition process controlled and optimized at each stage of the process for production of methane gas by anaerobic digestion of feed materials containing suitable organic materials at production rates and with production yields in excess of those which are possible with prior art processes.

While it is anticipated that the system and process of the present invention can be used to produce methane gas by anaerobic digestion of any feed material containing suitable organic materials, the process has not been practiced as of the date of filing of this patent application. Notwithstanding that the process has not been practiced, there is no reason to believe that any feed material which has been digested in prior art anaerobic digesters and by prior art anaerobic digestion processes is incapable of being used as a feed material for the system and process of the present invention. And, it is expected that the use of an individual digestion module or a group of digestion modules for each stage of the anaerobic decomposition process will enable the system and process of the present invention to digest feed materials not digestible in prior art anaerobic digesters and by prior art anaerobic digestion processes.

Figure 1:
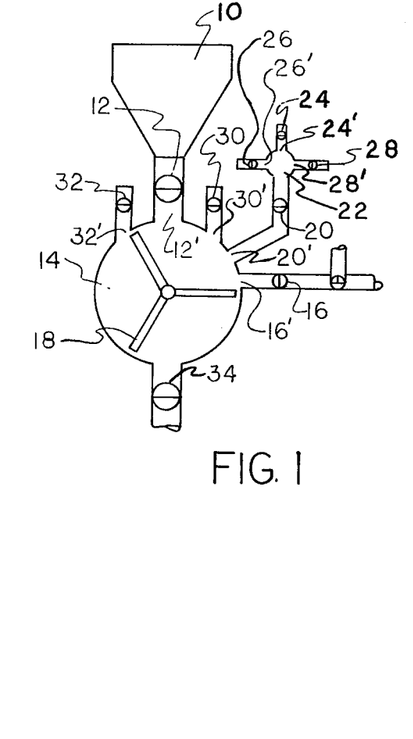
FIG. 1 is a schematic diagram of the feed material pre-treatment sub-system and the slurry production sub-system.

If necessary, inorganic materials, such as stones, cans, bottles and the like, are separated from the feed material to be digested. Referring now to FIG. 1, the feed material to be digested is first fed into the inlet of the feed material pre-treatment sub-system 10 for grinding and pulping in said sub-system. When the feed material has been ground and pulped to a suitable consistency, the valve 12 in the feed material inlet port 12' of the slurry preparation sub-system 14 is opened for transfer of the feed material into said sub-system for further processing. Valve 12 is closed and the valve 16 in the feed water inlet port 16' is opened and an appropriate amount of water or digestion effluent, or both, is introduced into the slurry preparation sub-system 14. Anaerobic conditions are maintained in the feed water inlet port 16' at all times.

When the appropriate amount of liquid has been added to the feed material, the valve 16 in the feed water inlet 16' is closed and the mixer 18 in the slurry preparation sub-system 14 is operated to mix the feed material until a slurry having the desired consistency is formed. When a slurry having the desired consistency has been formed, the valve 20 in the particle inlet port 20' of the slurry preparation sub-system 14 is opened to allow an appropriate quantity of suitable particulate material, such as an activated clay or an activated charcoal, to enter said sub-system and be mixed into the slurry. Before the particulate material is allowed to enter the slurry preparation sub-system, it is purged of oxygen in the particle purge chamber 22. This is accomplished by first opening the valve 24 in the particle inlet port 24' of said particle purge chamber and allowing an appropriate quantity of particulate material to flow into the particle purge chamber 22. The valve 24 is closed and a suitable purging gas, such as carbon dioxide, is introduced into the particle purge chamber 22 by opening the valve 26 in the purge gas inlet port 26'. The valve 28 in the purge gas outlet port 28' is then opened to allow the purging gas to force the oxygen in the particle purge chamber 22 out of said chamber through the purge gas outlet port 28'. When this purging process is complete, valves 26 and 28 are closed and the valve 20 in the particle inlet port 20' is opened as described hereinabove. At all times during the slurry preparation process, the valve 30 in the purge gas inlet 30' of the slurry preparation sub-system 14 and the valve 32 in the purge gas outlet 32' of said sub-system are in the open mode to allow a suitable purge gas, such as carbon dioxide, to force oxygen out of said sub-system through purge gas outlet 32'.

Figure 2:
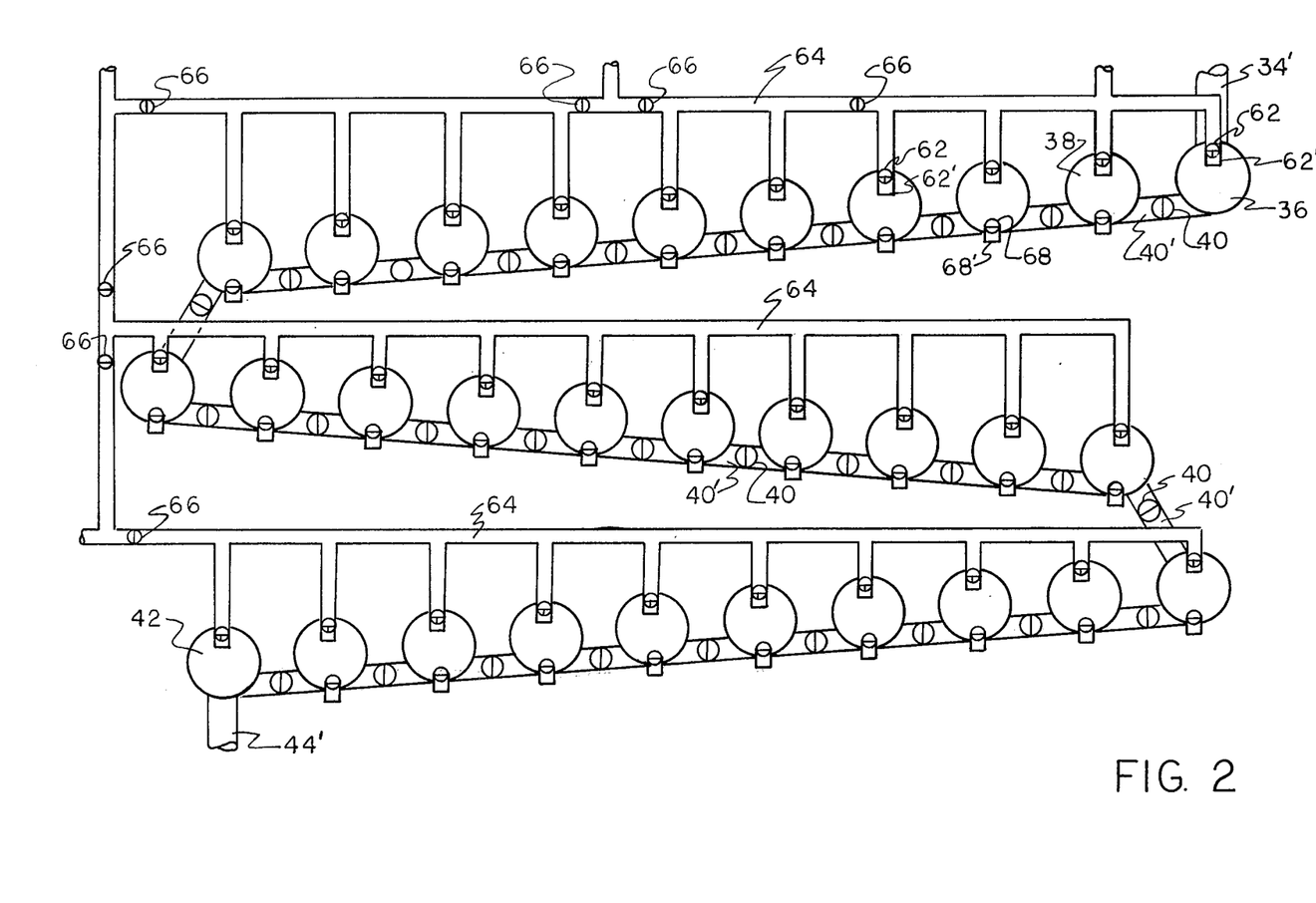
FIG. 2 is a schematic diagram of the anaerobic digestion sub-system and the gas collection sub-system.

Upon completion of slurry preparation, the valve 34 in the slurry inlet port 34' of the initial digestion module 36 is opened to allow the slurry to flow into said digestion module. Referring now to FIG. 2, the slurry in the initial digestion module 36 is retained in said digestion module for a predetermined retention time period. In the preferred embodiment, the slurry retention time period is 24 hours in each individual digestion module. After 24 hours, the slurry in the initial digestion module 36 is transferred to the next successive digestion module 38 by opening the valve 40 in the slurry transfer tube 40' connecting the initial digestion module 36 and the next successive digestion module 38 and allowing the slurry to flow into the next successive digestion module 38. When this transfer has been completed, the valve 40 in the slurry transfer tube 40' is closed and the valve 34 in the slurry inlet port 34' of the initial digestion module 36 is opened to transfer freshly prepared slurry to the initial digestion module 36. This transfer procedure is repeated at approximately 24-hour intervals by first transferring digesting slurry from the oldest charged digestion module to the next successive empty digestion module. Or, if all of the digestion modules of the anaerobic digestion sub-system are charged, digested slurry from the last digestion module is first transferred to the sludge separation sub-system. In either case, the resulting empty digestion module is then charged with slurry transferred from the preceding digestion module and the transfer procedure repeated until all the digestion modules in the sub-system have been charged.

The total number of digestion modules in the anaerobic digestion sub-system is dependent upon both the nature of the feed materials to be digested and the operating temperature for each individual module. In general, the number of digestion modules can be expected to fall within a range of five to forty modules. A minimum of two digestion modules would be required for a multi-stage anaerobic decomposition process. In the preferred embodiment, each digestion module is a cylindrically shaped reaction vessel, such as a conventional fifty-five gallon drum, positioned on its side with its slurry inlet port at a slightly lower elevation than the slurry outlet port of the preceding digestion module. In addition, each digestion module is positioned on an incline with its slurry outlet port slightly lower than its slurry inlet port. Each digestion module is insulated and heated by conventional means. Conventional means are used to control the temperature of each module. Of course, containers of alternate sizes and geometrical shapes can be used for the individual digestion modules without altering either the function of modules or the function of the system and process of the present invention. For example, under certan circumstances, it may be desirable to use long tubes or pipes as digestion modules. If large systems are constructed, below ground poured concrete containers may be desirable.

Figure 3:
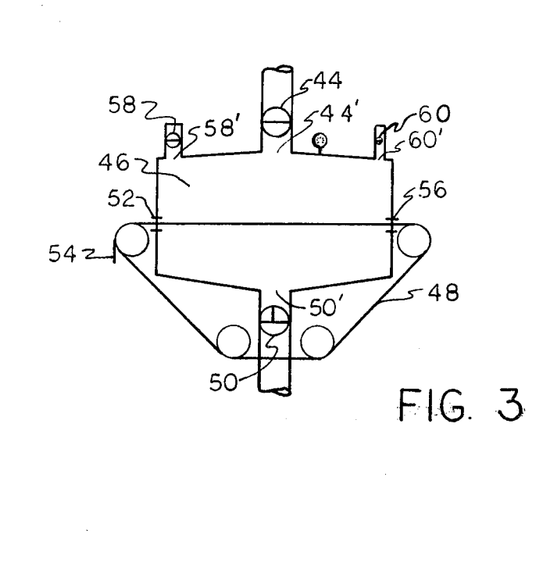
FIG. 3 is a schematic diagram of the sludge separation sub-system.

Referring now to FIG. 3, the slurry in the final digestion module 42 of the anaerobic digestion sub-system is discharged from said sub-system by opening the valve 44 in slurry inlet port 44' of the sludge separation sub-system 46. At this time, anaerobic digestion is essentially complete and the digested slurry flows on to the top surface of the movable screen 48. Most of the solid material in the digested slurry is trapped on the top surface of the movable screen 48 while the liquid in the slurry filters through said movable screen and drops to the bottom of the sludge separation sub-system 46. From time to time, this liquid effluent is discharged from the sludge separation sub-system 46 by opening the valve 50 in the liquid effluent discharge port 50'. The solid material which remains on the top surface of the movable screen 48 exits the sludge separation sub-system 46 through the door 52 for removal from the top surface of said movable screen by the fixed scrapper 54. When door 52 opens, door 56 opens to enable the movable screen 48 to move freely through the sludge separation sub-system 46. During operation of the sludge separation sub-system 46, the valve 58 in the purge gas inlet port 58' and the valve 60 in the purge gas outlet port 60' are maintained in an open mode to allow a suitable purge gas, such as carbon dioxide, to flow into the sludge separation sub-system 46 and force oxygen out of said sub-system through the purge gas outlet port 60'.

During normal operation of the system of the present invention, carbon dioxide gas, methane gas and low molecular weight organic liquids are produced in the individual digestion modules by anaerobic digestion of feed materials containing suitable organic materials. It is anticipated that most of the carbon dioxide will be produced in the first several digestion modules and that most of the methane will be produced in the last several digestion modules. It is likely that a gaseous mixture of both carbon dioxide and methane will be produced in the intermediate digestion modules. A three-way valve 62 is provided in the gas sampling and discharge port 62' located at the top of each digestion module. The three-way valve 62 can be used by the operator of the system to sample the gases produced in the digestion module. In this manner, it is possible to know the quality and quanity of the gaseous product produced in each digestion module for process control purposes and to avoid unnecessary mixing and subsequent separation of different gases. And, of course, when the three-way valve 62 is maintained in the appropriate mode, a substantial portion of the gases produced in the digestion module rise from the module and flow into the gas collection sub-system 64. A plurality of valves 66 are provided in the gas collection sub-system 64 to divert the gases which rise from the digestion modules to approriate locations for storage or subsequent processing, or both.

A valve 68 is provided in the sample port 68' near the bottom of each digestion module to enable the operator of the system to sample the digesting slurry for chemical and physical analysis. In this manner, it is possible to understand and control the anaerobic digestion processes in each individual digestion module. Furthermore, with the valve 68 in the appropriate mode, the sample port 68' can be used for adding appropriate materials for adjusting the pH of the digesting slurry and microbes, enzymes, catalysts and other materials suitable for enhancing methane gas production and controlling the anaerobic digestion processes to the digesting slurry in each digestion module. In addition, immobilized microbes and enzymes can be used to enhance methane gas production in selected digestion modules. Porous organic or inorganic materials, or both, can be used to line the interior surface of selected digestion modules to provide a means for either immobilizing and retaining, or retaining previously immobilized, microbes and enzymes in the particular digestion modules. Alternatively, solid shapes of such materials can be placed inside the particular digestion module.

Figure 4:
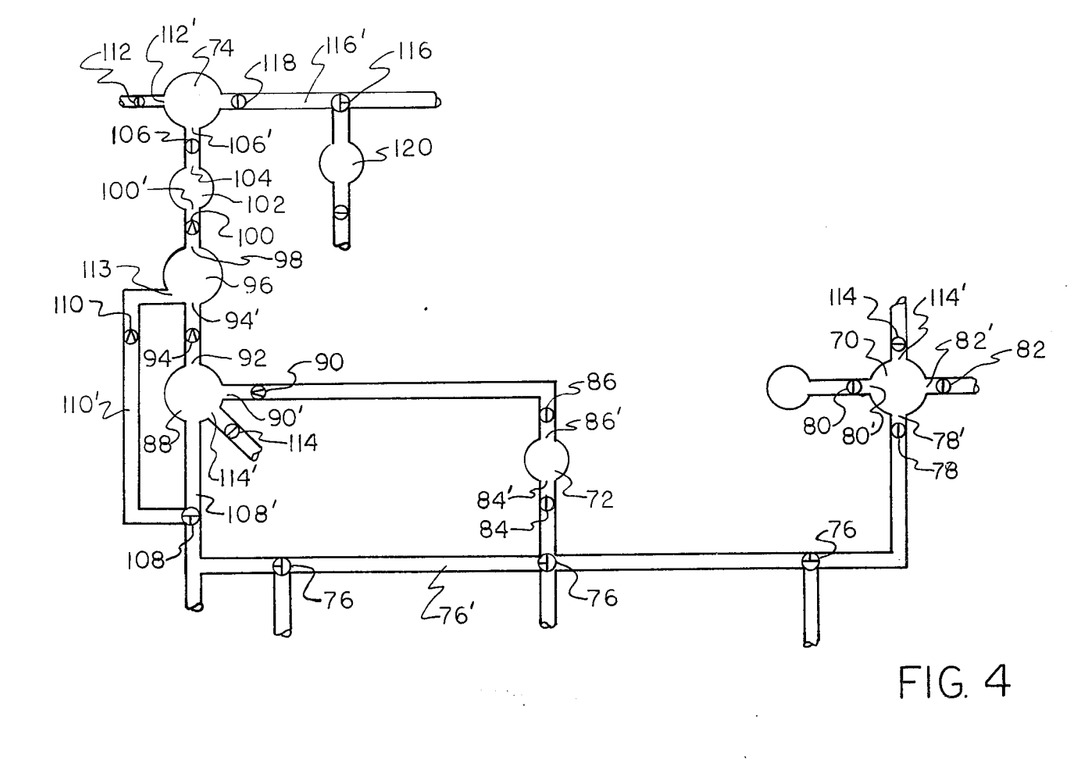
FIG. 4 is a schematic diagram of the gas storage sub-system.

Referring now to FIG. 4, the gases generated in each digestion module and collected in the gas collection sub-system 64 are either stored in the carbon dioxide storage vessel 70, the mixed gases storage vessel 72 or the methane storage vessel 74, or some combination thereof, in the gas storage sub-system. The valves 76 in the gas transfer tube 76' of the gas storage sub-system are used to control the flow of gases to the desired storage location or locations. The essentially pure carbon dioxide gas collected from the first several digestion modules of the anaerobic digestion sub-system is routed through the gas transfer tube 76' and into the carbon dioxide storage vessel 70. To accomplish this routing the valve 78 in the carbon dioxide inlet port 78' of said storage vessel is maintained in an open mode. Carbon dioxide produced in the various digestion modules, collected in the gas collection sub-system and stored in the carbon dioxide storage vessel 70 of the gas storage sub-system can be used for manufacture of dry ice by opening the valve 80 in the carbon dioxide outlet port 80' of said storage vessel and allowing the carbon dioxide to flow to a conventional dry ice manufacturing system. Alternatively, carbon dioxide from the carbon dioxide storage vessel 70 can be used as a purging gas for the anaerobic digestion system by opening the valve 82 in the carbon dioxide outlet port 82'of said storage vessel and allowing the carbon dioxide to flow through conventional gas transfer piping to the various purge gas inlet ports described hereinabove.

The mixed gases collected from the intermediate digestion modules of the anaerobic digestion sub-system are routed through the gas transfer tube 76' and into the mixed gas storage vessel 72. To accomplish this routing the valve 84 in the mixed gas inlet port 84' of the mixed gas storage vessel 72 is maintained in an open mode. To separate the mixed gases, the valve 86 in the mixed gas outlet port 86' of the mixed gas storage vessel 72 is opened to allow the mixed gases to flow to a conventional scrubber or condenser 88 for removal of carbon dioxide from the mixture. A one-way valve 90 in the mixed gas inlet port 90' of said scrubber or condenser prevents backflow of these gases. Alternatively, the mixed gases can be routed directly to the scrubber or condenser 88 by maintaining the three-way valve 108 in the mixed gas inlet port 108' in the appropriate mode. The cleaned gas from the scrubber or condenser 88 is essentially methane with a trace of hydrogen sulfide. This gas flows out of the scrubber or condenser 88 through gas outlet port 92, through one-way valve 94 in the gas inlet port 94' of the hydrogen sulfide scrubber 96, and into said hydrogen sulfide scrubber.

Following removal of hydrogen sulfide, the methane flows out of the hydrogen sulfide scrubber 96 through methane outlet port 98, through one-way valve 100 in the methane inlet port 100' of the gas compressor 102, and into said gas compressor. The methane is compressed in the gas compressor 102 to reduce its volume and flows out of the methane outlet port 104 of said gas compressor, through the one-way valve 106 in the methane inlet port 106' of the methane storage vessel 74, and into said storage vessel. For safety purposes, a conventional odorant, such as ethyl mercaptan, is added to the methane gas in the methane storage vessel 74 by opening the valve 112 in the odorant inlet port 112' of said storage vessel.

The essentially pure methane gas collected from the last several digestion modules of the anaerobic digestion sub-system is routed through the gas transfer tube 76' and into the methane storage vessel 74. To accomplish this routing, the three-way valve 108 in the mixed gas inlet port 108' of the scrubber or condenser 88 is maintained in the appropriate mode for flow of the methane through the one-way valve 110 in the scrubber or condenser by-pass tube 110' and into the hydrogen sulfide scrubber 96 through gas inlet port 113. Following removal of hydrogen sulfide, the methane gas flows into the methane storage vessel 74 in the manner described hereinabove.

The carbon dioxide from the scrubber or condenser 88 is transferred to the carbon dioxide storage vessel 70 by opening the valve 114 in the gas transfer tube 114'. The methane in the methane storage vessel 74 is transferred to a utilization system by producing the valve 116 in the gas transfer tube 116'. The pressure regulator 118 in the gas transfer tube 116' maintains a constant methane pressure of five to ten psi. The methane gas can either be passed through a preferential gas absorbing media 120 to reduce its moisture content or used directly as a fuel.

Figure 5:
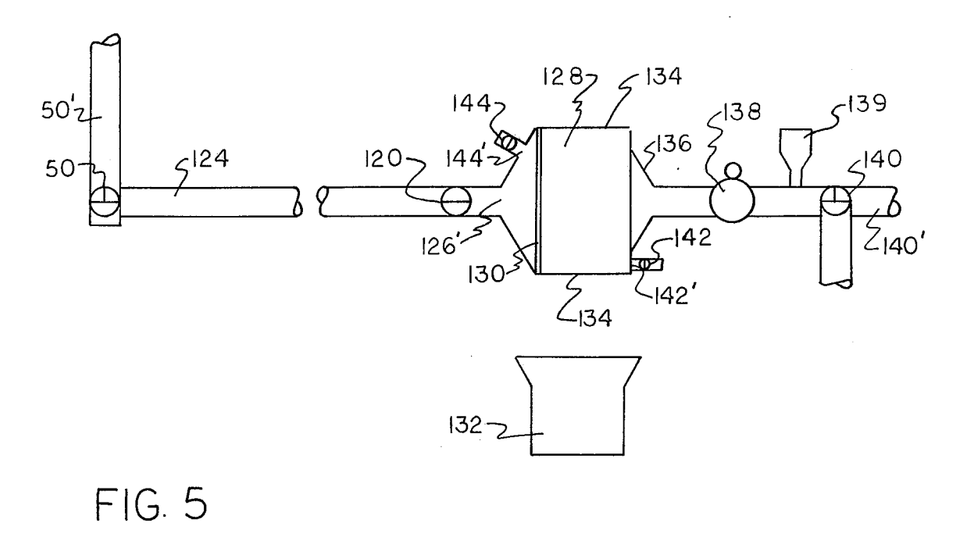
FIG. 5 is a schematic diagram of the particle separation sub-system.

Referring now to FIG. 5, the liquid effluent discharged from the sludge collection sub-system 46 enters the effluent liquid transfer pipe 124 through the valve 50 in the liquid effluent outlet port 50', flows through the liquid effluent transfer pipe 124 and the valve 126 in the liquid effluent inlet port 126' of the particle separation sub-system 128, and enters said sub-system. The particles are trapped on the suface of a filter 130 and collected in a hopper 132 and out gassed in an appropriate apparatus to release the adsorbed and absorbed methane. A pair of doors 134 are provided for removal of the filter 130 for cleaning or replacement. Other conventional precipitation means, such as electrostatic preparation or magnetic preparation can be used instead of the filter means described.

The liquid effluent which passes through the filter 130 exits the particle separation sub-system 128 through the liquid effluent outlet port 136 and enters the liquid effluent pump 138 where necessary pressure is applied to transfer the liquid effluent to the slurry preparation sub-system 14. After the liquid effluent is forced out of the liquid effluent pump 138, it can be sampled and analyzed by an appropriate analyzer to determine its soluble solids content. This enables the operator to recycle an appropriate volume of liquid effluent for mixing with water and feed materials in the slurry preparation sub-system 14 to achieve an optimum concentration of dissolved solids in the slurry. The three-way valve 140 in the liquid effluent transfer tube 140' is used by the operator to either direct the flow of liquid effluent to the slurry preparation sub-system 14 or discharge the liquid effluent from the system for uses external to the system. During these particle separation and liquid effluent transfer operations, the valve 142 in the purge gas inlet 142' and the valve 144 in the purge gas outlet 144' of the particle separation sub-system 128 are maintained in an open mode to allow a suitable purge gas, such as carbon dioxide, to force oxygen out of said sub-system through the purge gas outlet 144'.

Components, equipment, materials fabrication methods and construction methods necessary to make and use the system of the present invention are well known in the art and are described in numerous publications; such as Ram Bux Singh, Bio-Gas Plant, Mothers Print Shop, P. O. Box 70, Hendersonville, N.C. (1975); L. John Fry, Methane Gas Digesters for Fuel and Fertilizer, The New Alchemy, P.O. Box 432, Woods Hole, Mass. (1973); and Leslie M. Auerbach, A Homeside Power Unit: Methane Generator, Alternative Energy Systems, Madison, Ct. (2d Ed. 1974). Each of these cited publications are hereby incorporated by reference.

While the present invention has been disclosed in connection with the preferred embodiment thereof, it should be understood that there may be other embodiments which fall within the spirit and scope of the invention as defined by the following claims.

We claim:

1. A process for production of methane gas by anaerobic digestion of feed materials containing suitable organic materials, comprising the steps of:
   (a) grinding and pulping the feed material in a feed material pre-treatment sub-system;
   (b) transferring the ground and pulped feed material to a slurry preparation sub-system and purging oxygen from that sub-system;
   (c) mixing appropriate volumes of either water or liquid effluent, or both, with said ground and pulped feed material in said slurry preparation sub-system until a slurry having a desired consistency is formed;
   (d) adding particulate material to said slurry in said slurry preparation sub-system for subsequent adsorption and absorption of methane produced by anaerobic decomposition of said slurry;
   (e) transferring said slurry to the initial digestion module in an anaerobic digestion sub-system comprised of a plurality of digestion modules and retaining said slurry in said initial digestion module for a predetermined period of time sufficient to produce carbon dioxide, methane, and low molecular weight organic liquids from the anaerobic digestion of said slurry;
   (f) transferring said slurry from said initial digestion module to the next successive digestion module and retaining said slurry in said digestion module for the same predetermined period of time;
   (g) repeating steps (a) through (e);
   (h) transferring the slurry from the last charged digestion module to the next successive digestion module and retaining said slurry in said digestion module for the same predetermined period of time;
   (i) repeating step (h) until each of said digestion modules has been charged with slurry;
   (j) repeating steps (a) through (e);
   (k) anaerobically digesting said slurry to produce essentially carbon dioxide in the first several digestion modules, a mixture of carbon dioxide and methane in the intermediate digestion modules, and essentially methane in the last several digestion modules simultaneously collecting gases produced in each of said digestion modules and transferring said gases to a carbon dioxide storage location, a mixed carbon dioxide and methane storage location, and a methane storage location, respectively;
   (l) transferring the slurry from the last digestion module to a sludge separation sub-system and removing substantially all of the solid material having larger particle sizes from said slurry for subsequent use;
   (m) transferring liquid effluent from said sludge separation sub-system to a particle separation sub-system and removing particulate material having adsorbed and absorbed methane from said liquid effluent;
   (n) transferring appropriate volumes of liquid effluent to said slurry preparation sub-system;
   (o) repeating steps (l) through (n).

2. A process for production of methane gas as recited in claim 1, wherein said predetermined time period is twenty-four hours.

3. A process for production of methane gas as recited in claim 1, wherein said particulate material for absorption and adsorption of methane produced in said anaerobic digestion sub-system is activated charcoal or activated clay.

4. A system for production of methane gas by anaerobic digestion of feed materials containing suitable organic materials, comprising:
   (a) a feed material pre-treatment sub-system for grinding and pulping feed materials containing suitable organic materials;
   (b) a slurry preparation sub-system including means for adding either water or recycled liquid effluent, or both, to the pre-treated feed materials and mixing until a slurry having a desired consistency has been formed, said sub-system having a means for purging oxygen therefrom and means for adding particulate material for adsorbing and absorbing methane;
   (c) an anaerobic digestion sub-system for digestion of said slurry comprising a plurality of digestion modules, arranged either in series or parallel, or a combination thereof, each having a slurry inlet port, a slurry outlet port, a gas sampling and discharge port having a three-way valve positioned therein at a location external to said digestion module and a slurry sample and material addition port having a three-way valve positioned therein at a location external to said digestion module, means for transferring digesting slurry from each of said digestion modules to the next successive digestion module, and means for heating and controlling the temperature of each digestion module;
   (d) a gas collection sub-system connected to each of said gas discharge ports for collection of the gases produced in each of said digestion modules said gas collection subsystem including a plurality of valves to divert the gas produced in the first several digestion modules to a carbon dioxide storage vessel, the gas produced to the intermediate digestion modules to a carbon dioxide and methane storage vessel, and the gas produced in the last several digestion modules to a methane storage vessel;
   (e) a gas storage sub-system for storage of said gases including a carbon dioxide storage vessel, a carbon dioxide and methane storage vessel, and a methane storage vessel;
   (f) a sludge separation sub-system for removal of solid material from the digested slurry discharged from said anaerobic digestion sub-system, said sub-system having a means for purging oxygen therefrom;
   (g) a particle separation sub-system for removal of said particulate material from the liquid effluent discharged from said sludge separation sub-system, said sub-system having a means for purging oxygen therefrom; and
   (h) means for determining the soluble solid content of the liquid effluent discharged from said sludge sepration sub-system and recycling an appropriate volume of said liquid effluent for preparation of slurry in said slurry production sub-system.

5. A system for production of methane gas as recited in claim 4, wherein said means for transferring digesting slurry from each of said digestion modules to the next successive digestion module in said anaerobic digestion sub-system comprises means for positioning each of said digestion modules such that its slurry outlet port is maintained at a slightly higher elevation than the slurry inlet port of the next successive digestion module and a plurality of slurry transfer tubes, each connecting the slurry outlet port of one digestion module to the slurry inlet port of the next successive digestion module and each having a valve positioned therein.

6. A system for production of methane gas as rected in claim 4, further comprising a porous material in at least one of said digestion modules for retaining immobilized microbes, enzymes, catalysts and the like in said digestion module or for immobilizing and retaining microbes, enzymes, catalysts and the like in said digestion module.

* * * * *

UNITED STATES PATENT AND TRADEMARK OFFICE
CERTIFICATE OF CORRECTION

PATENT NO. : 4252901

DATED : Feb. 24, 1981

INVENTOR(S) : David J. Fischer; Richard M. Narske; John C. Thomas; Edward J. Worthington, Jr.

It is certified that error appears in the above-identified patent and that said Letters Patent are hereby corrected as shown below:

In the Description of the Preferred Embodiment, Column 10, Line 34, the word "precipitation" should be --separation--; the word "preparation" divided on Lines 34 and 35 should be --precipitation--; and the word "preparation" on Line 35 should be --precipitation--.

In Claim 4 (h), Line 63, the word "sepration" should be --separation--.

Signed and Sealed this

Nineteenth Day of May 1981

[SEAL]

Attest:

RENE D. TEGTMEYER

Attesting Officer

Acting Commissioner of Patents and Trademarks